US012678218B2

(12) United States Patent
Blocher et al.

(10) Patent No.: US 12,678,218 B2
(45) Date of Patent: Jul. 14, 2026

(54) INSULATION OF A SHAFT

(71) Applicant: KARL STORZ SE & Co. KG,
Tuttlingen (DE)

(72) Inventors: Martin Blocher, Tuttlingen (DE); Sven Axel Grüner, Tuttlingen (DE); Judith Holzer, Tuttlingen (DE); Daniel Kärcher, Tuttlingen (DE); Dominik Längle, Tuttlingen (DE); Robin Merz, Tuttlingen (DE); Janosz Schneider, Tuttlingen (DE); Sven Schneider, Tuttlingen (DE); Jochen Stefan, Tuttlingen (DE); Tobias Unger, Tuttlingen (DE)

(73) Assignee: KARL STORZ SE & Co. KG,
Tuttlingen (DE)

( * ) Notice: Subject to any disclaimer, the term of this patent is extended or adjusted under 35 U.S.C. 154(b) by 562 days.

(21) Appl. No.: 17/500,530

(22) Filed: Oct. 13, 2021

(65) Prior Publication Data

US 2022/0110672 A1 Apr. 14, 2022

(30) Foreign Application Priority Data

Oct. 14, 2020 (DE) ..................... 10 2020 126 968.4

(51) Int. Cl.
*A61B 17/00* (2006.01)
*A61B 17/29* (2006.01)
*A61B 18/14* (2006.01)
*A61B 18/00* (2006.01)

(52) U.S. Cl.
CPC .. *A61B 18/148* (2013.01); *A61B 2017/00526* (2013.01); *A61B 2017/00929* (2013.01); *A61B 2017/2901* (2013.01); *A61B 2018/00083* (2013.01)

(58) Field of Classification Search
CPC ........ A61B 18/148; A61B 2017/00929; A61B 2017/2901; A61B 2018/00083; A61B 18/1445; A61B 2018/00101; A61B 2017/00526; B32B 2307/304; B28B 19/0038; F16C 2202/24; F16L 59/02; F16L 58/1045; F16L 58/109; F16L 59/028
See application file for complete search history.

(56) References Cited

U.S. PATENT DOCUMENTS

| | | | |
|---|---|---|---|
| 2001/0031964 A1 | 10/2001 | Gentelia et al. | |
| 2013/0231682 A1 | 9/2013 | Baerwinkel et al. | |
| 2014/0100561 A1* | 4/2014 | Biadillah ........... | A61B 18/1492 606/33 |

(Continued)

FOREIGN PATENT DOCUMENTS

| | | |
|---|---|---|
| DE | 10 2015 205457 A1 | 9/2016 |
| DE | 10 2016 007232 A1 | 12/2017 |

*Primary Examiner* — Joanne M Rodden
*Assistant Examiner* — Dana Stumpfoll
(74) *Attorney, Agent, or Firm* — McGlew and Tuttle, P.C.

(57) ABSTRACT

An electrically insulated shaft (30) of a microinvasive instrument or for a microinvasive instrument includes an electrically conductive shaft component (40) with an outer surface (44) and an insulation tube (50) formed of an electrically insulating material, which encloses the shaft component (40) and covers the outer surface (44) of the shaft component (40). The insulation tube (50) is melted or welded onto the outer surface (44) of the shaft component (40).

6 Claims, 3 Drawing Sheets

(56)                References Cited

U.S. PATENT DOCUMENTS

2019/0142501 A1 *  5/2019  Hetzel .................. A61B 18/148
                                                           607/116
2020/0000512 A1 *  1/2020  Heiliger ............. A61B 18/1445

* cited by examiner

Fig. 1
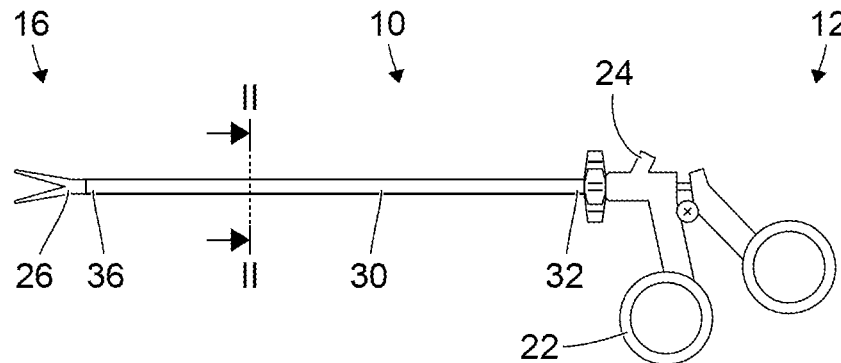
Fig. 2    II-II
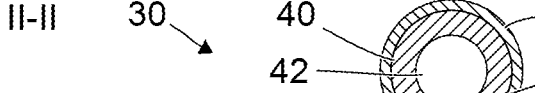
Fig. 3
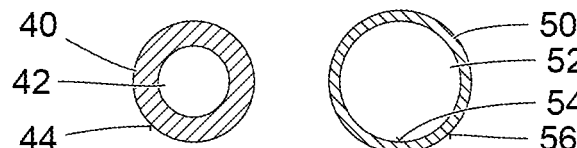
Fig. 4
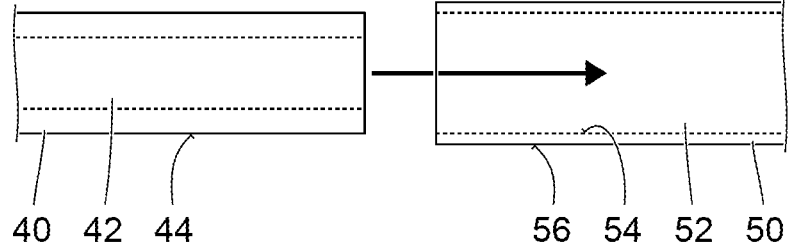

Fig. 7

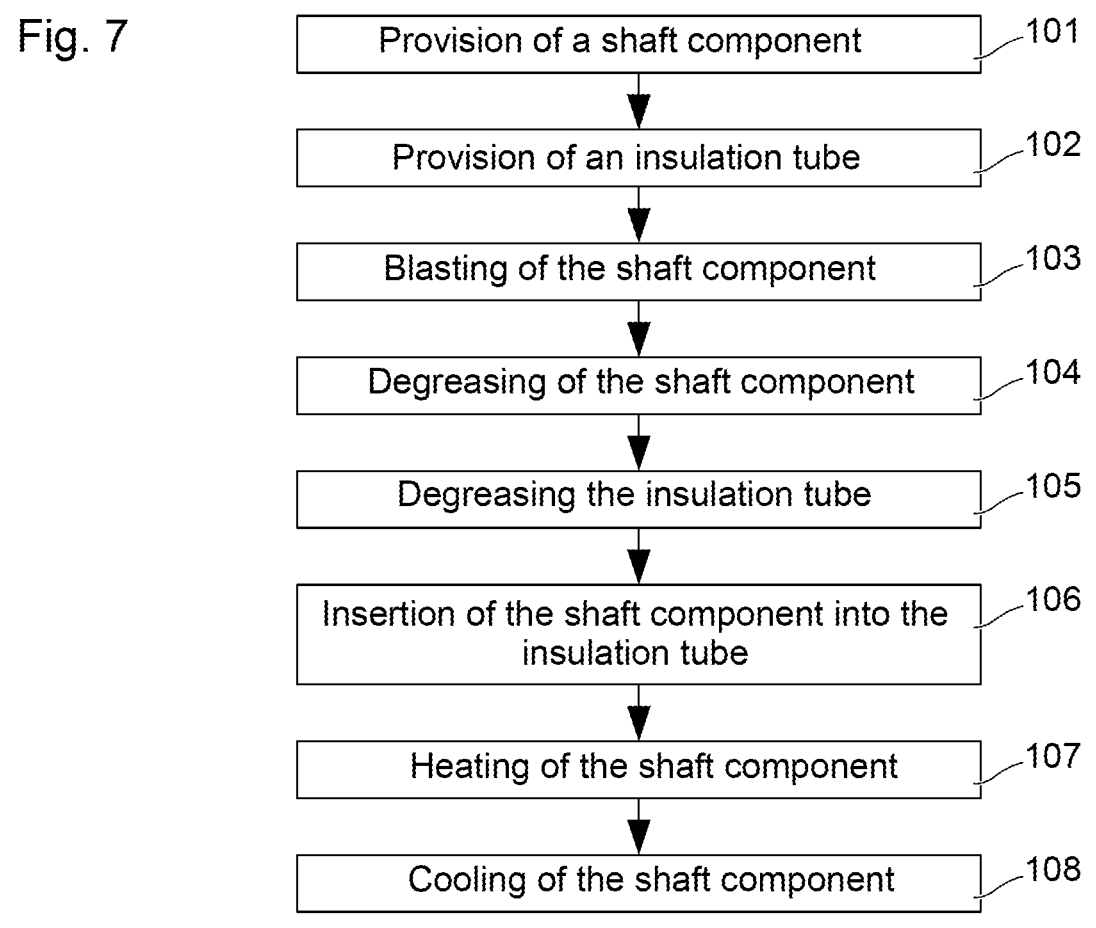

| Provision of a shaft component | 101 |

↓

| Provision of an insulation tube | 102 |

↓

| Blasting of the shaft component | 103 |

↓

| Degreasing of the shaft component | 104 |

↓

| Degreasing the insulation tube | 105 |

↓

| Insertion of the shaft component into the insulation tube | 106 |

↓

| Heating of the shaft component | 107 |

↓

| Cooling of the shaft component | 108 |

INSULATION OF A SHAFT

CROSS REFERENCE TO RELATED APPLICATIONS

This application claims the benefit of priority under 35 U.S.C. § 119 of German Application 10 2020 126 968.4, filed Oct. 14, 2020, the entire contents of which are incorporated herein by reference.

TECHNICAL FIELD

The present invention pertains to an electrically insulated shaft, to a microinvasive instrument with an electrically insulated shaft and to a process for manufacturing an electrically insulated shaft.

TECHNICAL BACKGROUND

High-frequency alternating currents are used in electrosurgical or high-frequency surgical procedures in order to heat and thus to alter, especially coagulate, weld or cut tissues. The alternating voltage and the electrical power necessary for this are usually fed at least partially via electrosurgical instruments. Electrical insulation is necessary in order to clearly define the desired electric circuit and to avoid short circuits and other undesired paths of current and the risks and damage to the patient, to the medical staff and to devices, which are associated therewith.

Instruments intended for use in microinvasive surgery (often also called minimally invasive surgery) have, as a rule, a long, thin shaft. This long and thin shaft shall have, as a rule, the smallest possible cross section and at the same time be electrically insulated for electrosurgical applications. An outer insulating layer in the form of a heat-shrinkable sleeve is frequently applied, but it possesses unsatisfactory mechanical properties. Other electrically insulating coatings are, as a rule, complicated and correspondingly expensive.

SUMMARY

One object of the present invention is to create an improved electrically insulated shaft, an improved microinvasive instrument with an electrically insulated shaft and an improved process for manufacturing an electrically insulated shaft.

Embodiments of the present invention are based on the idea of pulling an insulating layer in the form of a prefabricated insulation tube consisting of (formed of) an electrically insulating material over the electrically conductive, namely, especially metallic shaft component and of subsequently welding or melting the inner surface of the insulation tube to the outer surface of the shaft component by heating the shaft component.

An electrically insulating layer of a microinvasive instrument or for a microinvasive instrument comprises an electrically conductive shaft component with an outer surface and an insulation tube consisting of (formed of) an electrically insulating material, which insulating material encloses the shaft component and covers the outer surface of the shaft component, wherein the insulation tube is melted or welded as an originally tubular blank onto the outer surface of the shaft component to provide a melted or welded connection of the insulation tube to the shaft component.

The electrically insulated shaft may be a permanent component of a microinvasive instrument, which cannot be taken apart or can be taken apart only partially, or an independent component, which can be completely and non-destructively separated from other components and be mechanically connected to these again, especially without the use of a tool. As an alternative, the electrically insulated shaft may be intended and configured for use in a microinvasive instrument, which can be taken apart or which cannot be taken apart.

The electrically insulated shaft is especially long and thin, the length of the electrically insulated shaft being at least 5 times or at least 10 times or at least 20 times the diameter of the electrically insulated shaft. The insulation tube extends especially at least over half or at least over three quarters or at least over nine tenths of the length of the electrically insulated shaft. The shaft component may be configured tabularly with a lumen or with a plurality of lumens arranged in parallel or as a massive rod.

The insulation tube may be melted or welded onto the outer surface of the shaft component at its ends in strip-shaped areas, which fully enclose the shaft component in a ring-shaped manner. This can prevent the entry of fluids or solids into an intermediate space between the insulation tube and the surface of the shaft component. As an alternative, the insulation tube may be melted or welded over its entire surface onto the outer surface of the shaft component.

The melting or welding on of the insulation tube, which is already consequently in the form of a tubular blank originally, to the surface of the shaft component can make possible a robust mechanical connection of the insulation tube as an insulating layer to the shaft component. The connection by connection in substance between the insulation tube and the surface of the shaft component can also be carried out with a markedly reduced effort as, for example, a bonding. The formation of an insulating layer from an originally tubular blank makes it possible, furthermore, to use electrically insulating materials, which have markedly advantageous mechanical properties, for example, compared to a heat-shrinkable sleeve.

A microinvasive instrument comprises a shaft, as it is being described here, a manipulating device at a proximal end of the shaft for manually guiding and controlling the microinvasive instrument and a tool at a distal end of the shaft.

The microinvasive instrument is intended and configured, for example, for gripping, squeezing, closing and/or cutting a vessel or other tissues. The tool has for this purpose especially two or more mouth parts or branches, which can be moved relative to one another and have, for example, gripping surfaces or cutting edges, at the distal end.

A microinvasive instrument, as it is being described here, is configured especially as an electrosurgical instrument, wherein the shaft component is a part of an electric circuit for transmitting electric power or an electrical signal.

The shaft component, which assumes above all mechanical functions, is consequently intended and configured at the same time as a part of an electric circuit, in order to eliminate the need for an additional electric line and to make possible a smaller cross section. The proximal end or a proximal area of the shaft component is connected in an electrically conductive manner to an electrical plug contact or to another electrically conductive terminal at the proximal end of the microinvasive instrument. The distal end or a distal area of the shaft component is connected in an electrically conductive manner especially to one or more mouth parts or branches of the tool.

A process for manufacturing an electrically insulated shaft for a microinvasive instrument comprises the provision of a shaft component with an outer surface, provision of an insulation tube consisting of (formed of) an electrically insulating material, arrangement of the shaft component in an insulation tube, heating of the shaft component to a melting point or to a transition temperature or to a softening point of the electrically insulating material of the insulation tube and cooling of the shaft component and of the insulation tube.

The process is suitable and intended especially for manufacturing an electrically insulated shaft, as it is being described here. An electrically insulated shaft, as it is being described here, is manufactured especially by means of a process as it being described here.

The above-described process steps are carried out in the order described. In particular, the insulation tube consisting of (formed of) the electrically insulating material is provided as a tubular blank before the shaft component is arranged in the insulation tube. Consequently, the insulation tube is not formed only on the outer surface of the shaft component.

The cross section of the lumen of the insulation tube and the cross section of the shaft component are selected especially to be such that no or only a very narrow gap remains between the inner surface of the insulation tube and the outer surface of the shaft component. The shaft component is heated, in particular, only to the extent and only just long enough that the inner surface of the insulation tube will melt and form a welded connection by connection in substance with the outer surface of the shaft component after cooling.

In a process as it is being described here, the outer surface of the shaft component is, furthermore, treated especially by blasting with a solid blasting material (an abrasive material) prior to the arrangement of the shaft component in the insulation tube.

The blasting with a solid blasting material is commonly also called sandblasting, technically also compressed air blasting with a solid blasting material (abrasive material) or sandblasting or abrasive blasting. The abrasive material is in the form of fine granules in a solid state of aggregation. For example, sand, blast furnace slag, glass granules, corundum, steel, plastic granules, nut shells or soda with suitable grinding finenesses is used as an abrasive material.

The blasting with a solid abrasive material can increase the roughness and hence the surface area of the outer surface of the shaft component and improve the connection by connection in substance between the insulation tube and the shaft component.

In a process as it is being described here, the outer surface of the shaft component is, in particular, degreased, furthermore, before the shaft component is arranged in the insulation tube.

The degreasing of the outer surface of the shaft component is carried out especially by means of a plasma. As an alternative, it is possible, for example, to use a solvent.

Further, the inner surface of the insulation tube is, in particular, degreased in a process as it is being described here before the shaft component is arranged in the insulation tube.

The degreasing of the inner surface of the insulation tube is carried out especially by means of plasma. As an alternative, it is possible, for example, to use a solvent, which does not dissolve the electrically insulating material of the insulation tube.

In a process as it is being described here, the heating of the shaft component comprises especially the generation of a location- and time-dependent temperature profile along the shaft component with a maximum of the temperature profile at or above a melting point or a transition temperature or a softening point of the electrically insulating material of the insulation tube, wherein the position of the maximum of the temperature is moved along the shaft component.

The melting point or transition temperature or softening point of the electrically insulating material of the insulation tube is consequently exceeded at any location only within a predefined time period, and the area in which the melting point, the transition temperature or the softening point is reached or exceeded is moved along the shaft component in a predefined manner. The area in which the melting point or the transition temperature or the softening point is reached or exceeded is moved especially from one end of the shaft component at a variable or constant rate to the other end of the shaft component. As an alternative, the melting point or the transition temperature or the softening point is reached or exceeded, for example, at first in a middle area of the shaft component, and two areas, in which the melting point or the transition temperature or the softening point is reached or exceeded, are moved towards the ends of the shaft component one after another or simultaneously starting from this middle area.

The described fact that the melting point or the transition temperature or the softening point of the electrically insulating material is reached or exceeded in a time- and location-dependent manner causes that the entire insulation tube is not welded or melted simultaneously with the surface of the shaft component, but the location of the welding or melting to one another sweeps over the entire surface of the shaft component in a predefined manner. This can prevent, for example, the formation of gas bubbles and promote a completely full-area connection of the insulation tube to the shaft component.

In a process as it is being described here, the heating of the shaft component comprises especially the generation of an eddy current in the shaft component.

The eddy current is generated especially by means of an induction coil, which encloses the shaft component. A temperature profile with a maximum can be generated on the outer surface of the shaft component with an induction coil, which is shorter or much shorter than the shaft component. By moving the shaft component relative to the induction coil or of the induction coil relative to the shaft component, this temperature maximum can be moved along the shaft component.

The shaft component is especially a shaft tube with a lumen in a process as it is being described here, and the heating of the shaft component comprises a feeding of power to a heating device arranged in the lumen of the shaft tube and a movement of the heating device relative to the shaft tube along the shaft tube.

The heating device comprises, for example, an electrical heating resistor in a cylindrical housing, similar to a heating cartridge for other applications. A location- and time-dependent temperature profile with a maximum at or above a melting point or a transition temperature or a softening point of the electrically insulating material of the insulation tube can be generated by moving the heating device along the shaft tube.

Embodiments will be explained in more detail below on the basis of the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic view of a microinvasive electrosurgical instrument;

FIG. 2 is a schematic view of a cross section through a shaft of the microinvasive electrosurgical instrument from FIG. 1;

FIG. 3 is a schematic view of cross sections of components of the shaft shown in FIG. 2;

FIG. 4 is a schematic view of the components shown in FIG. 3 prior to an assembly;

FIG. 7 is a schematic flow chart of a process for manufacturing an electrically insulated shaft.

DESCRIPTION OF PREFERRED EMBODIMENTS

Figure 5:
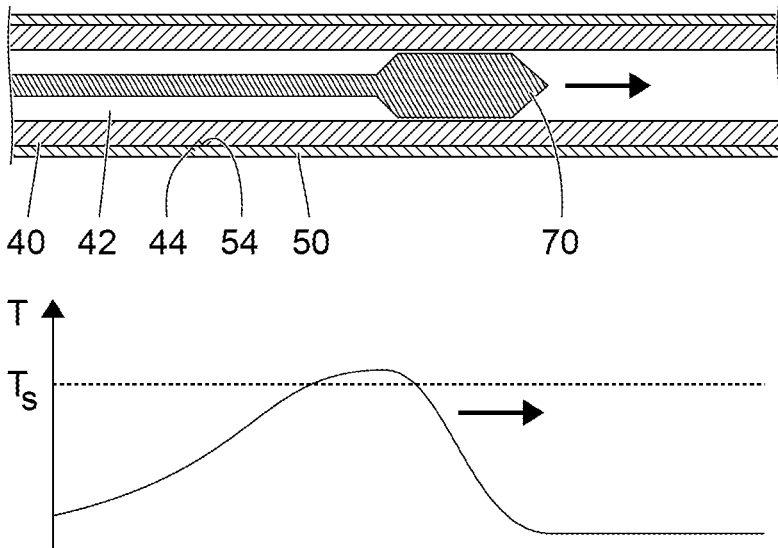
FIG. 5 is a schematic view of a longitudinal section through the shaft from FIGS. 1 through 4 and of a temperature profile.

Referring to the drawings, FIG. 1 shows a schematic view of a microinvasive electrosurgical instrument 10 with a proximal end 12 and with a distal end 16. The proximal end 12 of the microinvasive electrosurgical instrument 10 is formed by a manipulating device 22. The manipulating device 22 comprises in the example being shown a plurality of grip parts, which are movable relative to one another, and which make possible a manual control of one or more operating functions of the microinvasive electrosurgical instrument 10. An electrical plug contact 24 for feeding electric power is provided at the manipulating device 22.

The distal end 16 of the microinvasive electrosurgical instrument 10 is formed by a tool 26, in the example being shown by a gripping, squeezing and/or cutting tool. The microinvasive electrosurgical instrument 10 further comprises a shaft 30, whose proximal end 32 is connected to the manipulating device 22 and whose distal end 36 is connected to the tool 26.

FIG. 2 shows a schematic view, enlarged compared to FIG. 1, of a cross section through the shaft 30 of the microinvasive electrosurgical instrument 10 shown in FIG. 1. The section plane II-II of FIG. 2 is at right angles to the drawing plane of FIG. 1. The section plane II-II of FIG. 2 is suggested in FIG. 1.

The shaft 30 comprises an electrically conductive shaft component 40, which is configured with a lumen 42 as a shaft tube in the example being shown. For example, a force transmission device, not shown in FIG. 2, for transmitting a force from the manipulating device 22 to one or more movable mouth parts of the tool 26 of the microinvasive electrosurgical instrument 10 (cf. FIG. 1), may be arranged in the lumen 42.

The shaft 30 further comprises an insulation tube 50 consisting of (formed of) an electrically insulating material. The insulation tube 50 fully encloses the shaft component 40 in terms of the cross section. An inner surface 54 of the insulation tube 50 is welded or melted over the full area onto an outer surface 44 of the shaft component 40. An outer surface 56 of the insulation tube 50 forms the outer surface of the shaft 30.

FIG. 3 shows a schematic view, enlarged compared to FIG. 1, of cross sections of components of the shaft 30 from FIGS. 1 and 2, namely, of the shaft component 40 and of the insulation tube 50, prior to an assembly. The section planes according to FIG. 3 correspond to the section plane II-II of FIG. 2 or are parallel to this.

Not only the shaft component 40 consisting of the electrically conductive material, for example, surgical steel, but also the insulation tube 50 are in the form of a one-piece solid body each, namely a tube, already before the assembly into the shaft 30 shown in FIGS. 1 and 2. The insulation tube 50 encloses a lumen 52, whose cross section largely or completely corresponds to the external diameter of the shaft component 40, and into which the shaft component 40 will be inserted.

FIG. 4 shows another schematic view of the shaft component 40 and of the insulation tube 50 prior to the insertion of the shaft component 40 into the lumen 52 of the insulation tube 50. The drawing plane of FIG. 4 is at right angles to the drawing planes of FIGS. 2 and 3 and parallel to the drawing plane of FIG. 1. The contour of the lumen 42 of the shaft component 40 configured as a shaft tube and the contour of the lumen 52 of the insulation tube 50 are suggested each by broken lines. The relative movement necessary for the insertion of the shaft component 40 into the lumen 52 of the insulation tube 50 is suggested by an arrow.

The outer surface 44 of the shaft component 40 and the inner surface 54 of the insulation tube 50 may be pretreated prior to the insertion of the shaft component 40 into the lumen 52 of the insulation tube 50. In particular, the outer surface 44 of the shaft component 40 is blasted with a fine-grained, solid abrasive material. As a result, the outer surface 44 of the shaft component 40 can be roughened and its surface area can be enlarged. The outer surface 44 of the shaft component 40 can then be degreased, for example, by the action of a plasma. The inner surface 54 of the insulation tube 50 may also be degreased, for example, by the action of a plasma, prior to the insertion of the shaft component 40 into the lumen 52 of the insulation tube 50.

FIG. 5 shows a schematic view of a section through the shaft component 40 and through the insulation 50 from FIGS. 1 through 4 after the insertion of the shaft component 40 into the insulation tube. The section plane of FIG. 5 is parallel to the drawing planes of FIGS. 1 and 4, at right angles to the section planes of FIGS. 2 and 3 and contains the symmetry axis of the shaft component 40 and of the insulation tube 50.

A heating cartridge 70 is arranged in the lumen 42 of the shaft component 40 configured as a shaft tube. The heating cartridge 70 comprises an electrical heating resistor in a cylindrical housing, which can be moved with low friction in the lumen 42 of the shaft component 40. While electric power is being fed to the heating cartridge 70, the heating cartridge 70 is moved at the same time, as is indicated by an arrow in FIG. 5, through the lumen 42 of the shaft component 40 configured as a shaft tube. A temperature profile, which is suggested in the bottom part of FIG. 5, is generated thereby on the outer surface 44 of the shaft component 40. The temperature T is associated with the ordinate. The melting point TS of the electrically insulating material of the insulation tube 50 is suggested by a broken horizontal line.

Figure 6:
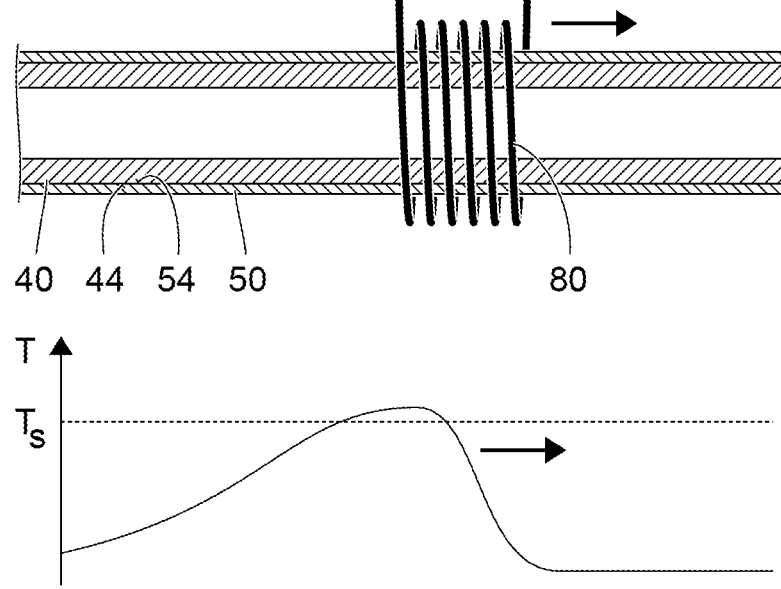
FIG. 6 is another schematic view of a longitudinal section through the shaft from FIGS. 1 through 5 and of a temperature profile.

As can be seen in the bottom right part of FIG. 6, the temperature of the shaft component 40 is originally low, especially markedly lower than the melting point TS. The power drain of the heating cartridge 70 increases the temperature T to above the melting point TS. The shaft component 40 cools again after the passage of the heating cartridge 70 and drops in the process rapidly below the melting point TS. During the short time period during which the temperature T on the outer surface 44 of the shaft component 40 and hence the temperature of the insulation tube 50 are also above the melting point TS on the inner surface thereof, the electrically insulating material of the insulation tube 50 wets the outer surface 44 of the shaft component 40. The electrically insulating material of the insulation tube 50 solidifies again during the cooling of the outer surface 44 of the shaft component 40 and hence also of the inner surface 54 of the insulation tube 50 to below the melting point TS. A connection of the insulation tube 50 to the shaft component 40 by connection in substance (a welded connection or melted connection) is formed thereby.

FIG. 6 shows a schematic view of another longitudinal section through the shaft component 40 and through the insulation tube 50 from FIGS. 2 through 5. The manner of representation, especially the position of the section plane, corresponds to that of FIG. 5. The shaft component 40 and the insulation tube 50 also correspond to the representations shown on the basis of FIGS. 2 through 5.

FIG. 6 shows an alternative form of the heating of the outer surface 44 of the shaft component 40, namely, heating by means of an induction coil 80. The shaft component 40 and the insulation tube 50 are arranged in the induction coil 80, and the induction coil 80 encloses the shaft component 40 and the insulation tube 50 in a ring-shaped manner. An alternating current in the induction coil 80 induces in the shaft component 40, close to the outer surface 44 thereof, an eddy current, which heats the shaft component ohmically based on the electrical resistance of the shaft component 40. The shaft component 40 and the insulation tube 50, on the one hand, and the induction coil, on the other hand, are moved relative to one another, as is suggested by an arrow in FIG. 6. A temperature profile similar to that described above on the basis of FIG. 5 is formed.

FIG. 7 shows a flow chart of a process for manufacturing an electrically insulating shaft. The process is especially suitable for use for manufacturing a shaft with features and properties shown on the basis of FIGS. 1 through 6. Reference numbers from FIGS. 1 through 6 will therefore be used below as an example.

A electrically conductive shaft component 40, especially a shaft tube, is provided in a first step 101. The shaft component 40 is manufactured, for example, from surgical steel. An insulation tube 50 consisting of an electrically insulating material is provided in a second step 102. The outer surface of the shaft component 40 and the inner surface of the insulation tube 50 have especially the same shape or are very similar. For example, the outer surface 44 of the shaft component 40 and the inner surface 54 of the insulation tube 50 are each circular cylindrical with identical or only slightly different diameters.

The outer surface 44 of the shaft component 40 is blasted with a fine-grained abrasive material in an optional third step 103. The outer surface 44 of the shaft component 40 is especially roughened in the process.

The outer surface 44 of the shaft component 40 is degreased in an optional fourth step. This is carried out especially by means of a plasma. A solvent or a surfactant may be used as an alternative.

The inner surface 54 of the insulation tube 50 is degreased in an optional fifth step 105. This is carried out especially by means of a plasma. A solvent, which does not dissolve the electrically insulating material of the insulation tube 50, or a surfactant may be used as an alternative.

The shaft component 40 is inserted into the lumen 52 of the insulation tube 50 in a sixth step 106.

In a seventh step 107, the outer surface 44 of the shaft component 40 is heated to a maximum temperature at or above a melting point or a transition temperature or a softening point of the electrically insulating material of the insulation tube 50. The inner surface 54 of the insulation tube 50 is thus also heated to the same temperature. The electrically insulating material of the insulation tube 50 melts or becomes free-flowing and it wets the outer surface 44 of the shaft component 40.

The heating 107 of the outer surface 44 of the shaft component 40 takes place, for example, by means of an eddy current, which is induced by a magnetic alternating field. If the shaft component 40 is a shaft tube with a lumen 42, it is possible, as an alternative, to arrange, for example, a heating cartridge in the lumen 42. In order to prevent gas bubbles from forming, the heating of the outer surface 44 of the shaft component 40 is not carried out, in particular, simultaneously, but, for example, such that the heating progresses from one end of the shaft component 40 to the other end thereof.

The outer surface 44 of the shaft component 40 and hence also the inner surface 54 of the insulation tube 40 are cooled in an eighth step 108. The temperature of the electrically insulating material drops on the inner surface 54 of the insulation tube 50 to below the melting point or transition temperature or softening point, and the electrically insulating material of the insulation tube 50 solidifies again completely, but doing so in a full-area connection by connection in substance with the outer surface 44 of the shaft component 40.

While specific embodiments of the invention have been shown and described in detail to illustrate the application of the principles of the invention, it will be understood that the invention may be embodied otherwise without departing from such principles.

REFERENCE NUMBERS

10 Microinvasive electrosurgical instrument
12 Proximal end of the microinvasive electrosurgical instrument 10
16 Distal end of the microinvasive electrosurgical instrument 10
22 Manipulating device at the proximal end 12 of the microinvasive electrosurgical instrument 10
24 Electrical plug contact at the manipulating device 22
26 Tool at the distal end 16 of the microinvasive electrosurgical instrument 10
30 Shaft of the microinvasive electrosurgical instrument 10
32 Proximal end of the shaft 30
36 Distal end of the shaft 30
40 Electrically conductive shaft tube as a shaft component of the shaft 30
42 Lumen of the shaft tube 40
44 Outer surface of the shaft tube 40
50 Insulation tube as an insulating layer of the shaft 30
52 Lumen of the insulation tube 50
54 Inner surface of the insulation tube 50
56 Outer surface of the insulation tube 50
70 Heating cartridge
80 Induction coil
101 First step (provision of the shaft component)
102 Second step (provision of an insulation tube)
103 Third step (blasting of the outer surface of the shaft component)
104 Fourth step (degreasing of the outer surface of the shaft component)

105 Fifth step (degreasing of the surface of the insulation tube)

106 Sixth step (insertion of the shaft component into the insulation tube)

107 Seventh step (heating of the shaft component)

108 Eighth step (cooling of the shaft component)

What is claimed is:

1. An electrically insulated shaft of a microinvasive instrument or for a microinvasive instrument, the electrically insulated shaft comprising:

an electrically conductive shaft component with an outer surface;

an insulation tube configured of an electrically insulating material, which encloses the shaft component and covers the outer surface of the shaft component, wherein the insulation tube is melted or welded as an originally tubular blank onto the outer surface of the shaft component to provide a melted connection or a welded connection of the insulation tube to the electrically conductive shaft component which is a connection in substance of an inner surface of the insulation tube with the outer surface of the electrically conductive shaft component that extends circumferentially around the shaft and extends axially along a length of the insulation tube, wherein the melted connection or the welded connection is configured by the insulation tube being heated to a temperature sufficient to melt or weld the inner surface of the insulation tube to the outer surface of the shaft component, wherein gas bubble formation is prevented in the melted connection or the welded connection and the melted connection or the welded connection is a full surface area connection, which is created with the inner surface of the insulation tube fused along the entire circumferential and axial extent of the outer surface of the shaft component, wherein the melted connection or the welded connection is a configuration with no gas bubble along the entire circumferential and axial extent based on a melted connection or the welded connection heat progression from one end of the shaft component to another end thereof.

2. A microinvasive instrument comprising:

an electrically insulated shaft comprising:

an electrically conductive shaft component with an outer surface;

an insulation tube configured of an electrically insulating material, which encloses the shaft component and covers the outer surface of the shaft component, wherein the insulation tube is melted or welded as an originally tubular blank onto the outer surface of the shaft component to provide a melted connection or a welded connection of the insulation tube to the shaft component which is a connection in substance of an inner surface of the insulation tube with the outer surface of the shaft component that extends circumferentially around the shaft and extends axially along a length of the insulation tube, wherein the melted connection or the welded connection is configured by the insulation tube being heated to a temperature sufficient to melt or weld the inner surface of the insulation tube to the outer surface of the shaft component, wherein gas bubble formation is prevented and a full surface area connection is created with the inner surface of the insulation tube fused along the entire circumferential and axial extent of the outer surface of the shaft component, wherein the melted connection or the welded connection is a configuration with no gas bubble along the entire circumferential and axial extent based on a melted connection or the welded connection heat progression from one end of the shaft component to another end thereof;

a manipulating device at a proximal end of the electrically insulated shaft for manually guiding and controlling the microinvasive instrument; and a tool at a distal end of the shaft.

3. A microinvasive instrument in accordance with claim 2, wherein the microinvasive instrument is configured as an electrosurgical instrument;

the shaft component is a part of an electric circuit for transmitting electric power or an electrical signal.

4. An electrically insulated shaft of a microinvasive instrument or for a microinvasive instrument, the electrically insulated shaft comprising:

an electrically conductive shaft component with an outer surface;

an insulation tube configured of an electrically insulating material, wherein the insulation tube is dimensionally stable, which encloses the shaft component and covers the outer surface of the shaft component, wherein the insulation tube is melted or welded as an originally tubular blank onto the outer surface of the shaft component to be configured as a melted connection or a welded connection of the insulation tube to the shaft component, which is a full surface area connection of an inner surface of the insulation tube with the outer surface of the shaft component that extends circumferentially around an entire circumferential extent of the shaft component and extends axially along the shaft component for an entire axial length of the insulation tube, wherein the melted connection or the welded connection is configured by the insulation tube being heated progressively, from one end of the shaft component to another end thereof, to a temperature sufficient to melt or weld the inner surface of the insulation tube to the outer surface of the shaft component, wherein gas bubble formation is prevented and a full surface area connection is created with the inner surface of the insulation tube fused along the entire circumferential and axial extent of the outer surface of the shaft component are configured as a structurally unified component, wherein the melted connection or the welded connection is a configuration with no gas bubble along the entire circumferential and axial extent based on a melted connection or the welded connection heat progression from one end of the shaft component to another end thereof.

5. An electrically insulated shaft according to claim 4, in combination with a manipulating device and a tool to form a microinvasive instrument, wherein:

the manipulating device is at a proximal end of the electrically insulated shaft for manually guiding and controlling the microinvasive instrument; and the tool is at a distal end of the shaft.

6. An electrically insulated shaft according to claim 5, wherein:

the microinvasive instrument is configured as an electrosurgical instrument;

the shaft component is a part of an electric circuit for transmitting electric power or an electrical signal.

* * * * *